United States Patent
Gardner

[11] Patent Number: 5,339,119
[45] Date of Patent: Aug. 16, 1994

[54] EYE PROTECTION DEVICE COMPRISING A FOAM RUBBER-LIKE RESILIENT INSERT MEMBER

[76] Inventor: Lawrence C. Gardner, 24 Elliott Rd., Sterling, Mass. 01564

[21] Appl. No.: 168,131

[22] Filed: Dec. 17, 1993

[51] Int. Cl.$^5$ ............................ G02C 1/00; A61F 9/02
[52] U.S. Cl. ................................ 351/158; 351/44; 351/62; 351/83; 351/155; 2/431; 2/435
[58] Field of Search ............... 351/158, 44, 51, 52, 351/155, 41, 62, 83, 154, 43; 381/68.5; 359/409, 815, 816; 362/103; 2/431, 432, 435, 411, 414, 425, 426, 433, 434, 439, 440, 442, 443, 444

[56] References Cited

U.S. PATENT DOCUMENTS

| | | | |
|---|---|---|---|
| 3,384,903 | 12/1965 | Malcom, Jr. | 2/434 |
| 3,952,331 | 4/1976 | Melville | 2/431 |
| 4,322,138 | 3/1982 | Minart | 351/155 |
| 4,405,212 | 9/1983 | Cooper | 351/83 |
| 4,654,899 | 4/1987 | Harris | 2/426 |
| 4,707,863 | 11/1987 | McNeal | 2/439 |
| 4,934,807 | 6/1990 | Bollé et al. | 351/62 |
| 5,146,623 | 9/1992 | Paysan et al. | 351/44 |
| 5,191,364 | 3/1993 | Kopfer | 351/62 |
| 5,243,711 | 9/1993 | Graham | 2/430 |
| 5,245,709 | 9/1993 | Shipcott | 2/425 |

FOREIGN PATENT DOCUMENTS

| | | | |
|---|---|---|---|
| 2623300 | 5/1989 | France | 351/154 |
| 0189113 | 11/1982 | Japan | 351/83 |
| 405095972 | 4/1993 | Japan | 2/426 |

Primary Examiner—William L. Sikes
Assistant Examiner—Huy Mai
Attorney, Agent, or Firm—William Nitkin

[57] ABSTRACT

An eye protection device in one embodiment composed of a foam rubber-like member having a front portion, first and second side portions, and first and second apertures therein for receipt of the lenses and frame of a pair of eyeglasses with the side earpieces of the pair of eyeglasses being passed through the first and second apertures in the first and second side portions. When worn, the foam rubber-like member is compressed against the wearer's face to create a seal between the device and the user's face. The foam rubber-like member can be adhered in a second embodiment to the rear of an outer shell having a front portion, first and second side portions, and first and second apertures defined in the front portion which first and second apertures of the outer shell are in alignment, respectively, with the first and second apertures in the foam rubber-like member; and the first and second side portions of the insert member are in alignment, respectively, with the first and second side portions of the foam rubber-like member to form a sturdy, eye protection device.

12 Claims, 3 Drawing Sheets

EYE PROTECTION DEVICE COMPRISING A FOAM RUBBER-LIKE RESILIENT INSERT MEMBER

BACKGROUND OF THE INVENTION

1. Field of the Invention

The device of this invention resides in the area of eye protection devices and more particularly relates to a structure which receives a pair of eyeglasses therein and acts as a protective shield around the eyeglasses and the area around the wearer's eyes.

2. Description of the Prior Art

Protective eyewear such as ski goggles and safety goggles are well known in the prior art which goggles, in some cases, are made of a hard, transparent plastic shell and can be large enough to fit over the user's eyes or user's prescription eyewear. Such goggles often provide for air circulation therethrough but can be bulky and uncomfortable to wear. Poor or improper circulation of air in ski goggles can cause fogging of the eyeglass lenses, especially problematic for skiers exhaling, and wind blowing around the eyeglasses and striking the eye can also cause tearing.

Other prior art protective devices for use with eyeglasses include foam rings retained by adhesive onto the inside of each lens of a pair of eyeglasses which foam rings press inwards and surround and protect the eyes of the wearer. Leather-like side shields are also available to cover the eyeglass earpiece/frame junction area to protect the eyes from wind blowing, and light shining from the sides of the eyeglasses.

SUMMARY OF THE INVENTION

It is an object of this invention to provide a generally soft, compressible, rubber-like structure with lens apertures and eyeglass receipt channel area provided therein for the receipt and engagement of the user's existing prescription eyeglasses or non-prescription eyewear, such as sunglasses, to provide a barrier around the area of the user's face enclosed by the structure of this invention against the elements such as wind, snow and rain or airborne particles yet still providing sufficient air circulation to minimize fogging of the lenses. The structure of this invention can be made of one foam component or of two components: an outer shell which can be made of a polyurethane material and a foam rubber-like insert member which components are joined together to form a unitary structure which structure receives the user's eyeglasses therein. The eye protection device of this invention can also be used in industrial and medical fields to protect the user's eyes from air-borne particles, chemicals, bodily fluids and the like.

DESCRIPTION OF THE PREFERRED EMBODIMENT(S)

Figure 1:
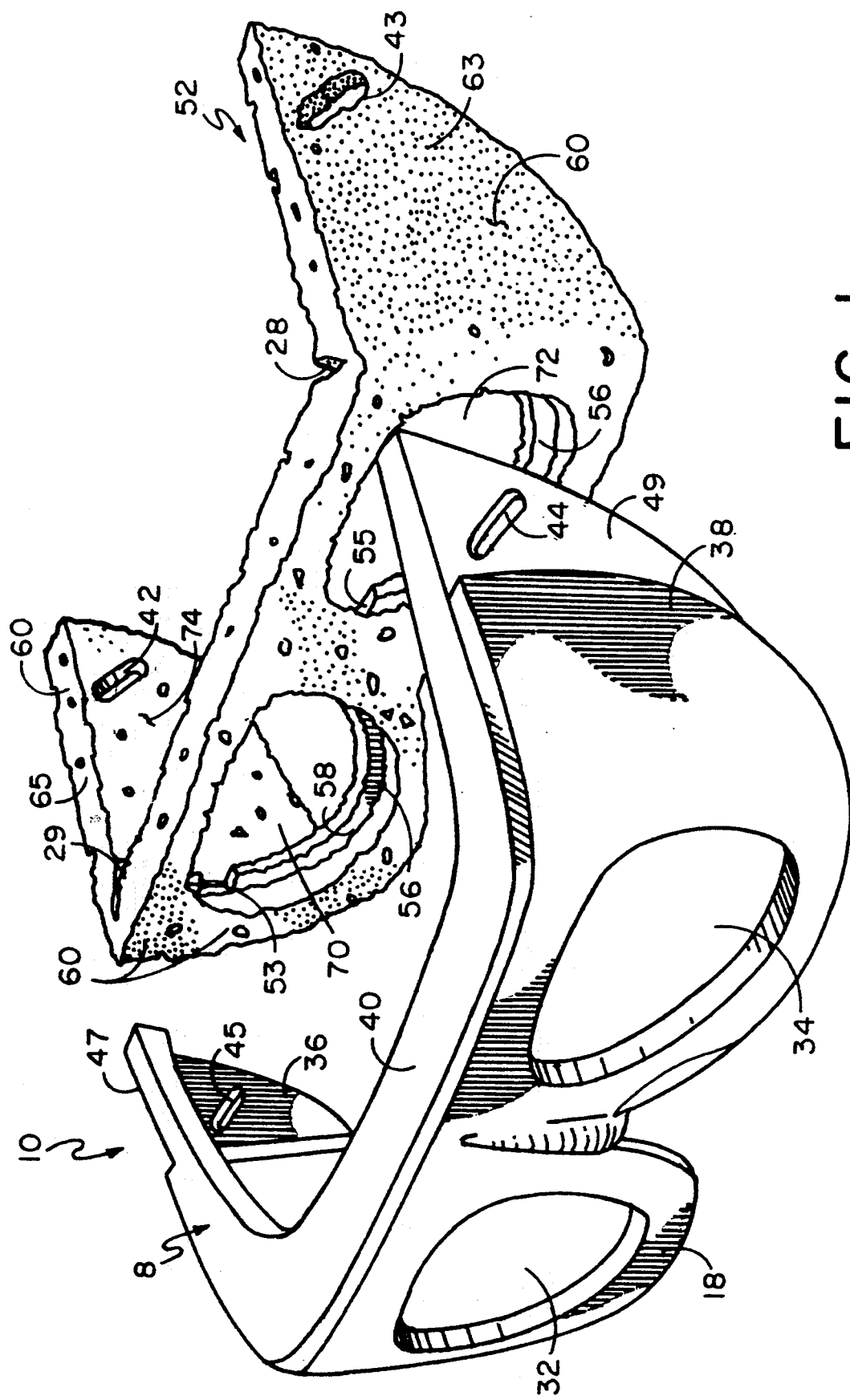
FIG. 1 illustrates a front perspective view of one embodiment of the device of this invention shown separated into its two component parts.

FIG. 1 illustrates a front perspective view of one embodiment of device 10 of this invention separated into two component parts. The device of this embodiment includes a resilient, rubber-like structure, being outer shell 8 composed of a front portion 18 and an inner side not seen in this view, rearwardly extending first and second side portions 36 and 38 having first and second lens apertures 32 and 34 defined, respectively, in front portion 18 which outer shell, in a preferred embodiment, can be made of a shape-retaining, but yet flexible, thin-molded polyurethane material such as Polyyou brand or equivalent. A foam rubber-like insert member 52 having a thickness and being extremely lightweight, soft and resilient, and having first and second insert member lens apertures 70 and 72, is adhered by adhesive 60 to the inner side of outer shell 8. Insert member 52 can be formed as a molded piece or formed from a flat piece of foam material which is then folded into shape. First and second V-shaped cuts 29 and 28 can be formed vertically in the inner side of insert member 52 to allow for the folding of first and second side members 65 and 63 to be easily bent rearwards if formed from a flat sheet of material. The overall shape of insert member 52, when positioned on the inner side of outer shell 8, corresponds to the general shape of outer shell 8 with their respective first and second lens apertures corresponding in shape and size and being in alignment with one another. Because of the thickness of insert member 52 which in a preferred embodiment can be 0.5 inch thick, insert member 52 is compressed against the wearer's face when the device is worn, filling in any spaces between the outer shell, the eyeglasses and the wearer's face, thereby preventing undesirable air flow around the eyeglasses such as might be encountered by one skiing, which air flow might otherwise enter from around the top, sides and/or bottom of the skier's eyeglasses to contact and irritate the eyes of the skier. The unitary structure of this invention offers nearly complete protection for the wearer's eyes and the portion of the wearer's face contacted by the structure.

In another embodiment of this invention, foam insert member 52 can be used alone without an outer shell to provide a low-cost foam eyeglass protection device. Although structurally weak and prone to tearing, such foam eyeglass protection device can be used one or a few times and then discarded. In some embodiments first and second vertical V-shaped cuts 29 and 28 can be made in rear of insert member 52 to help in folding first and second side members 65 and 63 rearward.

Figure 2:
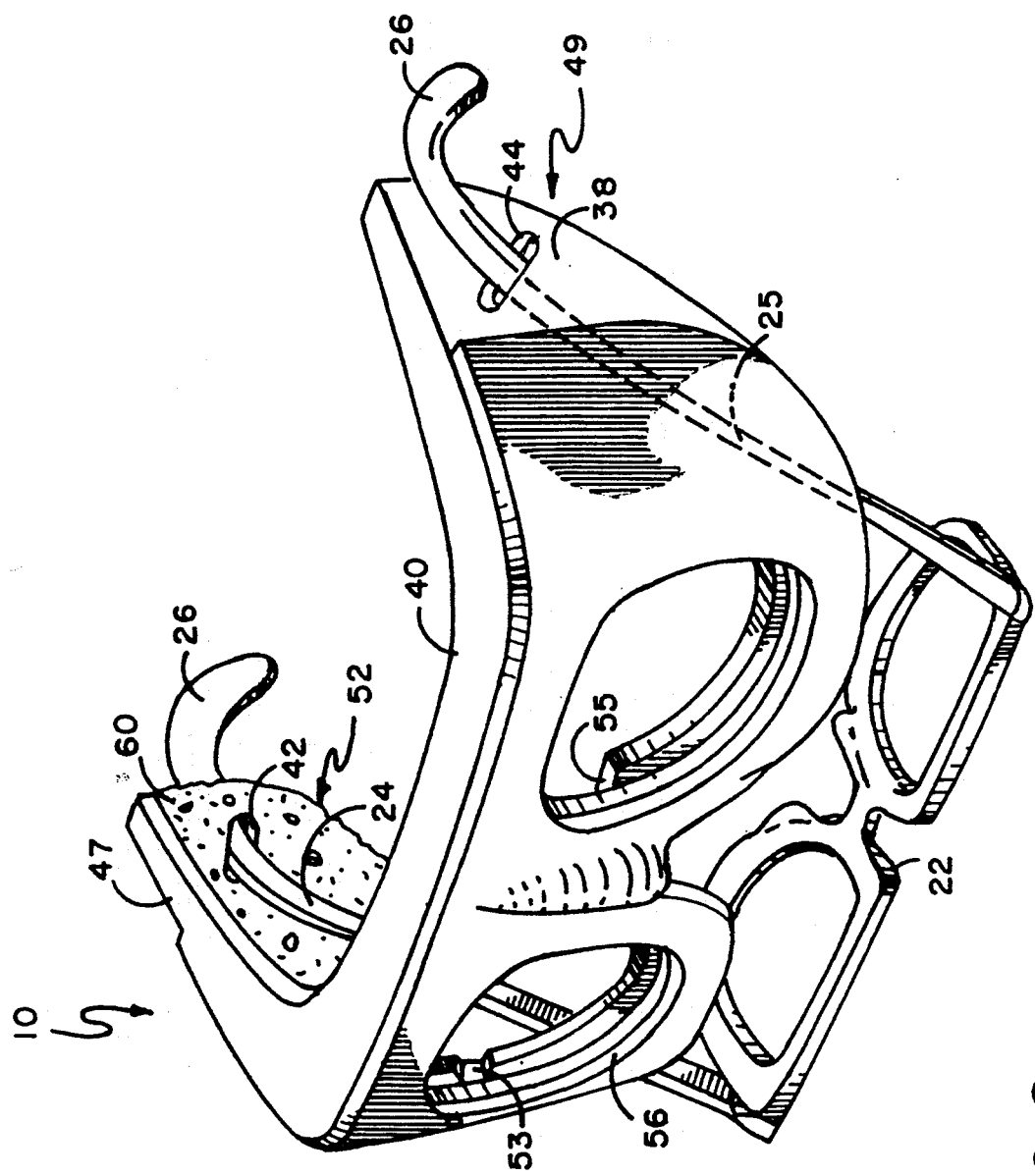
FIG. 2 illustrates a front perspective view of the structure of FIG. 1 with eyeglasses starting to be positioned therein, showing the foam member positioned within the outer shell.
Figure 3:
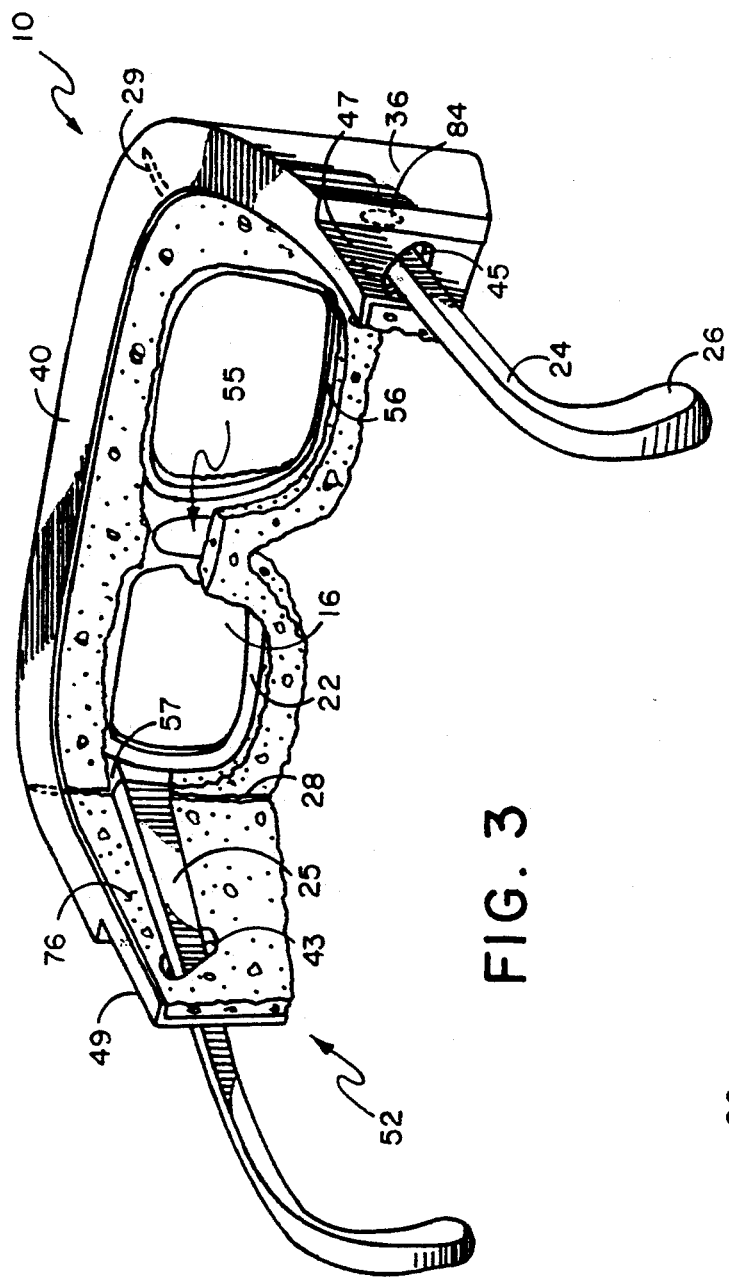
FIG. 3 illustrates a rear perspective view of the embodiment of FIG. 1 with eyeglasses installed therein.

Seen in FIG. 2 is the embodiment of FIG. 1 with the wearer's eyeglasses 22 starting to be positioned therein. First and second eyeglass earpieces 24 and 25 are first inserted, respectively, within first and second earpiece receipt apertures 42 and 43 in insert member 52 and then are passed through first and second outer shell earpiece apertures 45 and 44 formed, respectively, in first and second inset portions 47 and 49 of outer shell 8. The earpieces of eyeglasses 22, as seen in FIG. 2, are entered into first and second earpiece receipt apertures 42 and 43, not seen in this view, and into the corresponding first and second outer shell earpiece apertures 45 and 44, the former not seen in this view, from a position below the device and are pushed rearwards with first and second eyeglass earpieces 24 and 25 then contacting first and second inset portions 47 and 49, respectively, of the exterior of outer shell 8. Then the eyeglass lenses are positioned level with first and second lens apertures 32 and 34, and are then pushed forward toward front portion 18 of outer shell 8 to engage the frame within channels 56 formed within insert member 52 as described below. It should be noted that when eyeglass frames are mentioned within the context of this Specification, such eyeglass frames can include not only traditional eyeglass frames but also eyewear which has only upper frames and even eyeglasses which are frame-less where the rims of such eyeglass lenses can be positioned within the channels of the device of this invention. Channels 56 are defined within the sides of first and second insert member lens apertures 70 and 72 of insert member 52. Bridge slot 55 is formed in tile central portion of the inner side of insert member 52 to receive the eyeglasses' bridge, as best seen in FIG. 3; and earpiece hinge slots, such as first earpiece hinge slot 53 seen in FIG. 2, are formed on each side of channels 56 in the insert member to receive an eyeglass hinge. The equivalent earpiece hinge slot formed in the other side of the insert member is not seen in this view. In FIG. 3 one can see the frame and lenses 16 of eyeglasses 22 inserted within channels 56 formed in the device with first and second eyeglass ear pieces 24 and 25 having been inserted through first and second earpiece apertures such as second outer shell earpiece aperture 43 and such earpieces passed through first and second outer shell earpiece apertures 45 and 44, extending to a point where they can be hooked over the wearer's ears. The frame of the eyeglasses is securely held within channels 56 in which such frame is easily manually inserted because of the soft resiliency of the foam material of insert member 52. The bridge of the eyeglasses is held within bridge slot 55, and the eyeglass hinge members are accommodated in the earpiece hinge slots, such as first earpiece hinge slot 53 and second earpiece hinge slot 57 seen in FIG. 3, such that the eyeglasses are securely positioned because of the resiliency of the foam so that minimal amounts of air can pass between the glasses' frame and the structure of this invention. Upper portion 40 of the outer shell extends rearward, and first and second side portions 36 and 38 seen in FIG. 1 can have in one embodiment their bottoms extending angularly downward from the rear toward the front of the device to cover over the insert member and to give the device additional strength as well as providing a decorative molded exterior shape. The device of this invention with inserted eyeglasses is then placed on the head of the wearer with the rear of upper portion 40 in some cases coming in contact with the forehead of the wearer and the insert member contacting the wearer's face all around the eyeglasses, thus preventing air flow from reaching the wearer's eyes.

First and second eyeglass earpieces 24 and 25 extend, respectively, through first and second earpiece receipt apertures 42 and 43 and out first and second outer shell earpiece apertures 45 and 44 such that first and second eyeglass earpieces 24 and 25 somewhat compress the foam of the insert member, respectively, in first and second areas 74 and 76 seen in FIG. 1 and FIG. 2, respectively, and yet are held securely within insert member 52 and by outer shell 8 on each side. The earpiece receipt apertures 42 and 43 in insert member 52 and first and second outer shell earpiece apertures 45 and 44 can be disposed at a slant which configuration aids in the easy insertion of the earpieces from below.

Figure 4:
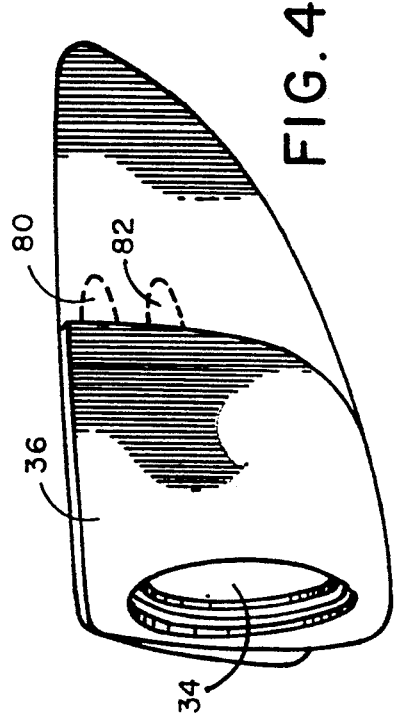
FIG. 4 illustrates a side view of an alternate embodiment of eyepiece apertures.

FIG. 4 illustrates an alternate embodiment of earpiece apertures. Since the rearwardly extending earpieces of eyeglasses can be positioned at different heights around the eyeglass frame with some earpiece members extending near the top of the frame while others extend midframe or lower, it is helpful to have selectable earpiece aperture openings such as openings 80 and 82 seen in FIG. 4 to accommodate such varied earpiece positionings. Seen surrounding these openings are perforations which are cut through the material of the device of this invention with the material in the aperture still left in place. Depending upon the height of his earpieces, the user would manually punch out the desired earpiece openings by tearing along the perforations and then insert the earpieces into such selected openings. By incorporating such perforations, tim device of this invention can be used by all eyeglass wearers regardless of the height positioning of their earpieces to their frame. Because of the nature of the insert member of this device, it will accommodate a wide variety of eye frame shapes but to accommodate the positioning of the rearwardly extending earpieces, it is desirable to provide for a selection of openings, in some instances of multiple openings, which the punchout openings of FIG. 4 have been found to be most suitable. Further the earpiece openings can be located on the side of the inset member, such as punch out aperture 84 seen in FIG. 3, so that the earpiece can be inserted through the inset side. Such earpiece aperature can also be formed from a single line of perforations which are separated by the user in the appropriate area to receive the earpiece.

The structure of this invention is economical to produce and, if desired, can be produced in its foam embodiment and/or foam/outer shell embodiment for disposable one-time usage. The device can bear advertising indicia on its outer sides, if desired, and can be manufactured in a variety of sizes, colors and attractive exterior shapes to accommodate the various styles, sizes and types of eyewear available while maintaining the basic structure and objectives of this invention.

Although the present invention has been described with reference to particular embodiments, it will be apparent to those skilled in the art that variations and modifications can be substituted therefor without departing from the principles and spirit of the invention.

I claim:

1. An eye protection device for use in combination with a pair of eyeglasses having a frame, a bridge, a first lens, a second lens, a first hinge member and a second hinge member, a first rearwardly extending side earpiece, and a second rearwardly extending side earpiece, said device to be worn on the face of a user, comprising:

a foam rubber-like member having a front portion having a first end and a second end, a rear inner side and a front outer side, said front portion having a first lens aperture and a second lens aperture defined therein, said foam rubber-like member having a first side portion and a second side portion with each side portion having an end, an inner side and an outer side, said first and second side portion being contiguous, respectively, with said first and second ends of said front portion and extending rearwards from said front portion, said foam rubber-like member having a thickness;

a first eyeglass frame receipt channel and a second eyeglass frame receipt channel, said first and second eyeglass frame receipt channels defined, respectively, around said first and second lens apertures in said foam rubber-like member; and a first eyeglass earpiece aperture and a second eyeglass earpiece aperture, said first and second eyeglass earpiece apertures defined, respectively, in said first and second side portions of said foam rubber-like member for said first and second eyeglass earpieces to pass therethrough.

2. The device of claim 1 wherein said thickness of said foam rubber-like member is sufficient to contact the user's face and be compressed thereagainst when said device is worn by said user to create a seal against the user's face to prevent wind, water or other environmental elements from contacting those areas of the user's face that are contacted by said device.

3. The device of claim 2 further including a bridge slot defined in said rear inner side of said foam rubber-like member between said first and second lens apertures, said bridge slot in communication with said first and second eyeglass frame receipt channels, said bridge slot to receive said bridge of said eyeglasses.

4. The device of claim 3 further including a first hinge slot and a second hinge slot, said hinge slots defined, respectively, in said rear inner side of said foam rubber-like member and positioned, respectively, at said first and second ends of said front portion, said first and second hinge slots to receive, respectively, said first and second hinge members of said eyeglasses.

5. The device of claim 4 further including a first V-shaped vertical cut and a second V-shaped vertical cut, said first and second V-shaped vertical cuts defined, respectively, in said inner side of said foam rubber-like member at said first and second ends of said front portion to aid in the rearward positioning of said first and second side portions.

6. An eye protection device for use in combination with a pair of eyeglasses having a frame, a bridge, a first lens, a second lens, a first hinge member and a second hinge member, a first rearwardly extending side earpiece, and a second rearwardly extending side earpiece, said device to be worn on the face of a user, comprising:

a rubber-like, outer shell having a front portion having a first end, a second end, an outer side, an inner side, a first lens aperture defined in said front portion of said outer shell, a second lens apertures defined in said front portion of said outer shell, said outer shell further laving a first side portion laving an end and a second side portion having an end, said first and second side portions extending rearwardly, respectively, from said first and second ends of said front portion;

a foam rubber-like, resilient insert member having a front portion laving a first end and a second end, a rear inner side and a front outer side, said front portion of said insert member laving a first lens aperture and a second lens aperture defined therein, said insert member laving a first side portion and a second side portion, each side portion having an end, an inner side and an outer side, said insert member having a thickness;

means to adhere said front outer side of said insert member to said inner side of said outer shell to form a unitary structure with said front portion of said outershell aligned with said front portion of said insert member, with said first and second eyeglass lens apertures of said outer shell aligned, respectively, with said first and second lens apertures of said insert member, and with said first and second side portions of said insert member aligned, respectively, with said first and second side portions of said outer shell; and a first outer shell eyeglass earpiece aperture and a second outer shell eyeglass earpiece aperture, said first and second eyeglass earpiece apertures defined, respectively, in said first and second side portions of said outer shell; and a first eyeglass earpiece insert member aperture and a second eyeglass earpiece insert member aperture, said first and second eyeglass earpiece insert member apertures defined, respectively, in said first and second side portions of said insert member, said first and second eyeglass earpiece insert members aligned, respectively, with said first and second eyeglass earpiece apertures of said outer shell for receipt of said first and second eyeglass earpieces.

7. The device of claim 6 wherein said thickness of said insert member is sufficient to contact said user's face and be compressed thereagainst when said device is worn to create a seal against the user's face to prevent wind, water or other environmental elements from contacting those areas of the user's face that are contacted by said device.

8. The device of claim 7 wherein said front portion of said outer shell further includes a rearwardly extending top portion.

9. The device of claim 7 further including a bridge slot defined in said inner side of said insert member between said first and second lens apertures of said insert member, said bridge slot to receive said bridge of said eyeglasses.

10. The device of claim 7 further including:

a first hinge slot and a second hinge slot, said first and second hinge slots defined, respectively, in said inner side of said insert member and positioned, respectively, at said first and second ends of said front portion of said insert member;

a first eyeglass frame channel and a second eyeglass frame channel, said first and second eyeglass frame channels formed, respectively, in said aligned first and second lens apertures of said insert member and said first and second lens apertures of said outer shell; and a first hinge slot and a second hinge slot, said first and second hinge slots defined, respectively, at said first and second ends on the rear inner side of said front portion of said insert member, said first and second hinge slots in communication, respectively, with said first and second eyeglass frame channels, said first and second hinge slots to receive said first and second hinge members of said eyeglasses.

11. The device of claim 7 further including a first V-shaped vertical cut and a second V-shaped vertical cut, said first and second V-shaped vertical cuts defined, respectively in said inner side of said insert member at said first and second ends of said front portion of said insert member.

12. The device of claim 7 further including a first inset portion and a second inset portion, said first and second inset portions defined, respectively, on said outer sides of said first and second side portions of said outer shell, said first and second inset portions positioned, respectively, around said first and second outer shell eyeglass earpiece apertures.

* * * * *